(12) United States Patent
Friedman et al.

(10) Patent No.: US 6,365,367 B1
(45) Date of Patent: Apr. 2, 2002

(54) ENVIRONMENTAL CHAMBER FOR THE ANALYSIS OF LIVE CELLS

(75) Inventors: Alexander L. Friedman; Stephen J. Gongaware, both of Pittsburgh; Albert H. Gough, Glenshaw, all of PA (US)

(73) Assignee: Cellomics, Inc., Pittsburgh, PA (US)

( * ) Notice: Subject to any disclaimer, the term of this patent is extended or adjusted under 35 U.S.C. 154(b) by 0 days.

(21) Appl. No.: 09/455,577

(22) Filed: Dec. 6, 1999

(51) Int. Cl.[7] .............................. C12Q 1/02; C12M 1/00; C12M 1/36
(52) U.S. Cl. .................. 435/29; 435/283.1; 435/286.6; 435/286.5; 435/287.1
(58) Field of Search ................ 435/29, 283.1, 435/286.6, 286.5, 287.1

(56) References Cited

U.S. PATENT DOCUMENTS

| 3,573,721 A | 4/1971 | Mason | 435/29 |
|---|---|---|---|
| 4,039,775 A | 8/1977 | Andra | 435/29 |
| 4,572,427 A | 2/1986 | Selfridge et al. | 435/29 |
| 4,974,952 A | 12/1990 | Focht | 435/29 |
| 5,149,654 A | 9/1992 | Gross et al. | 435/29 |
| 5,552,321 A | 9/1996 | Focht | 435/29 |
| 5,627,070 A | * 5/1997 | Gruenburg | 435/286.5 |
| 5,763,261 A | * 6/1998 | Gruenburg | 435/286.5 |
| 5,989,835 A | 11/1999 | Dunlay et al. | 435/29 |

FOREIGN PATENT DOCUMENTS

| EP | 0 238 313 | 9/1987 |
|---|---|---|
| EP | 0 955 097 | 11/1999 |
| JP | 01010977 | 1/1989 |
| WO | WO 97/45730 | 12/1997 |
| WO | WO 98/38490 | 9/1998 |

OTHER PUBLICATIONS

Payne, J. N., Cooper, J. D., MacKeown, S. T., Horobin, R. W., *J. Microscopy* 147, 329–335 (1987).
Boltz, R. C., Sirotina, A., Blake, T., Kath, G., Uhrig, B., McKeel, J. Quinn, C., *Cytometry* 17, 128–134 (1994).
Moores, S. L., Sabry, J. H., Spudich, J. A., *Proc. Natl. Acad. Sci USA* 93, 443–446 (1996).
Focht, D. C., *Nature Biotech.* 14, 361–362 (1996).

* cited by examiner

*Primary Examiner*—Louise N. Leary
(74) *Attorney, Agent, or Firm*—McDonnell Boehnen Hulbert & Berghoff; David S. Harper

(57) ABSTRACT

This invention provides environmental control devices and methods for live cell analysis. The devices of the invention combine a plate space that can hold specimen plates of a variety of sizes, gas flow control, and temperature control of the entire specimen plate.

20 Claims, 7 Drawing Sheets

X Watts/in² throughout heater region 1:   y Watts/in²
region 2:   >y Watts/in²

ENVIRONMENTAL CHAMBER FOR THE ANALYSIS OF LIVE CELLS

FIELD OF THE INVENTION

This invention is in the field of environmental control devices and methods for live cell analysis.

BACKGROUND OF THE INVENTION

High-content screening (HCS) is a cell-based screening method that yields temporal-spatial dynamics of cell constituents and processes. The information provided by HCS will alleviate bottlenecks in the drug discovery process by providing deep biological information. The assays associated with this method use either fixed or live cells. Fixed cells require no environmental conditioning because the biological information has been fixed in time. Live cells require the regulation of appropriate environmental conditions. The specific needs of a screen determine whether a live cell or fixed cell assay is advantageous. Fixing cells at a number of different time points can be time consuming. Therefore live cells assays save time when the kinetics of a cellular process need to be characterized. Furthermore live cell assays circumvent potential artifacts associated with a cell fixation process.

A number of environmental chambers have been described. For example, the Zeiss Environmental Chamber Incubator B (Carl Zeiss Inc., Thornwood, N.Y.) uses a moderately large (12.60" long (L)×8.66" wide (W)×3.54" high (H)) acrylic incubator housing that surrounds the mechanical stage for an Axiovert microscope series. Two heating control systems exist; one is for the microscope stage and one is for the circulated air. The relatively large volume of the chamber requires that the air be preheated so that it does not cool the stage. The concentration of $CO_2$ is controlled by mixing pure $CO_2$ with warmed air and directly sensing $CO_2$ concentration. The flow rate of the warmed air is also controlled.

The Olympus IX-IBM Incubator (Olympus America, Inc. Melville, N.Y.) uses a large (~24" Lx~18" Wx~18" H) transparent acrylic incubator housing that surrounds the mechanical stage, condenser, and mechanical manipulators, of the Olympus IX70 microscope. The single heating system consists of a heater mounted to one of the side walls of the incubator housing and a temperature probe mounted within the housing. There is no air circulation and no source of $CO_2$.

The Olympus IX-IBM $CO_2$ Incubator (Olympus America, Inc. Melville, N.Y.) uses a small (~7" Lx~7" Wx~2" H) transparent acrylic incubator housing that sits on the stage of an inverted microscope. Two heating systems exist: one for the circulated gas and one for the stage. Carbon dioxide is delivered to the chamber but its concentration is not controlled with a feedback system.

The Nikon Eclipse TE200 Incubator Accessory (Nikon, Inc. Melville, N.Y.) uses a large (~12" Lx18" Wx~18" H) transparent acrylic housing that surrounds the mechanical stage and condenser of the Eclipse TE200 Microscope. The temperature of the interior gas can be set to within 3° C. of the selected temperature. There is air circulation but no source of $CO_2$.

U.S. Pat. No. 4,974,592 describes an environmental chamber that only controls temperature, and limits the user to a single sample per experiment. It does not accommodate commercially available multi-sample microplates, nor does it have a gas flow system. Instead the chamber volume is fluid filled to allow control of the chamber solution via a flow-through system. It delivers heat through electrically conductive material that is part of the sample holder. The temperature control technique has also been patented (U.S. Pat. No. 5,552,321).

Descriptions of environmental chambers for maintaining biological cells during imaging for basic research are common in the scientific literature (See, for example, Payne et al., *J. Microscopy* 147, 329–335 (1987); Boltz et al., *Cytometry* 17, 128–134 (1994); Moores et al., *Proc. Natl. Acad. Sci USA* 93, 443–446 (1996); and Bioptechs, *Nature Biotech.* 14, 361–362 (1996)). These laboratory devices tend to be specifically designed for a narrow range of applications including imaging and maintenance of a few tens of cells in one micro-chamber, or imaging and maintaining a specific cell type (e.g. amoebae, bacteria, or mammalian cells). Some provide thermal regulation and some allow flow-through of solution.

None of the existing environmental chambers combine (a) a plate space that can hold specimen plates of a variety of sizes, including but not limited to commercially available microplates, microscope slides, and biological microchips; (b) gas flow control; and (c) control of the temperature of the entire specimen plate.

Thus, there remains a need in the art for environmental chambers that combine (a) a plate space that can hold specimen plates of a variety of sizes, including but not limited to commercially available microplates, microscope slides, and biological microchips; (b) as flow control; and (c) control of the temperature of the entire specimen plate.

SUMMARY OF THE INVENTION

The present invention fulfills the need in the art for environmental chambers that combine (a) a plate space that can hold specimen plates of a variety of sizes, including but not limited to commercially available microplates, microscope slides, and biological microchips; (b) gas flow control; and (c) control of the temperature of the entire specimen plate. In a preferred embodiment, the present invention provides an environmental chamber for live cell screening comprising a. a chamber housing comprising a plate space comprising a plate holder sized to permit insertion of a specimen plate, wherein the specimen plate comprises the bottom of the chamber housing when it is inserted into the chamber;

b. at least one gas inlet port;

c. a lid assembly comprising:
 1. a lid with a top and bottom surface, wherein the bottom surface overlays the plate space in the chamber housing when the lid is closed; and
 2. a heater attached to the top or the bottom of the lid.

In further preferred embodiments, the chamber further comprises one or more of a temperature control system, a gas flow control system, at least one gas inlet space, a chamber gasket, at least one gas outlet port, a lid cover, a lid insulator, and a lid latch. In a further preferred embodiment, the chamber housing, the lid and the lid cover are aluminum.

The present invention also provides methods for cell-based analysis comprising utilizing the environmental chamber of the invention for live cell analysis.

DETAILED DESCRIPTION OF THE INVENTION

Figure 1:
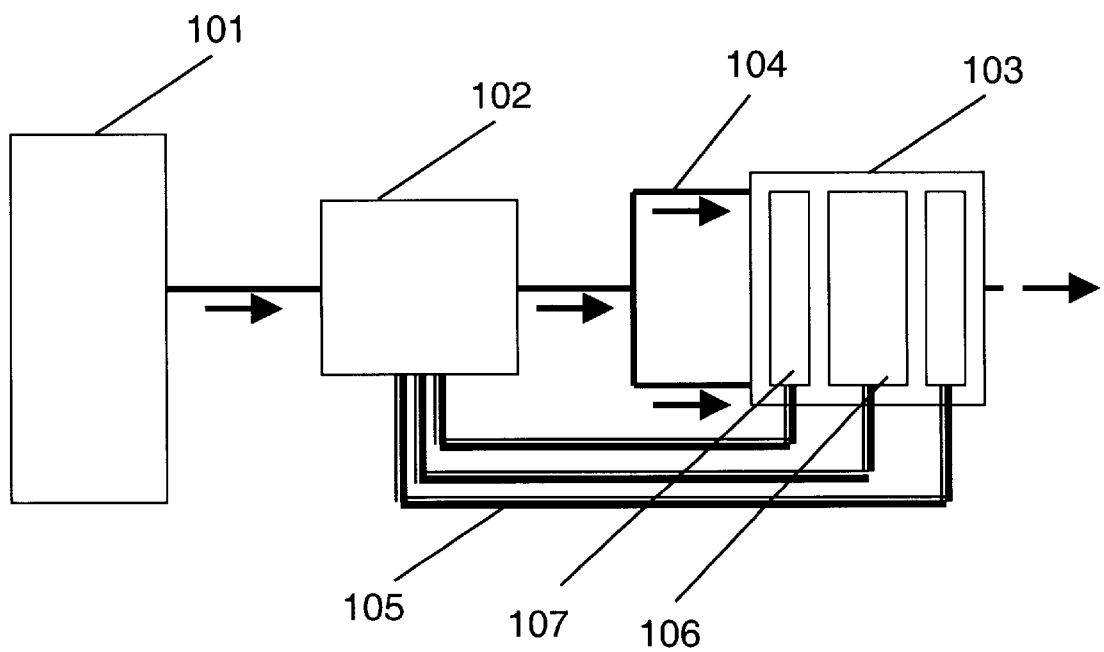
FIG. 1 is a block diagram schematic of a preferred embodiment of the environmental chamber, showing the gas flow and temperature control system.

All references cited are herein incorporated by reference in their entirety.

As used herein, the terms "environmental chamber" is synonymous with devices including, but not limited to, "incubators", "live cell chambers", and "live cell environmental chambers".

As used herein, the term "specimen" refers to any biological preparation that exists on the top or bottom surface of a specimen plate.

As used herein, the term "specimen plate" refers to any substrate that can be used for live cell analysis, including but not limited to commercially available microplates, slides, chambered cover glass, biological microchips, and microwells on a microplate, such as those described in U.S. patent application Ser. No. 08/865,341 filed May 29, 1997.

As used herein, the term "biological microchips" includes, but is not limited to DNA microarrays, protein microarrays, and cell-based microarrays, such as those disclosed in U.S. patent application Ser. No. 08/865,341 filed May 29, 1997.

As used herein, the term "plate holder" refers to the inner region of the chamber housing that secures the specimen plate for analysis.

As used herein the term "plate space" is defined as any space large enough to hold at least one specimen plate.

As used herein, the term "gas inlet port" is defined as any opening through which gas enters the plate space.

As used herein, the term "specimen plate seal" refers to any means to decrease the rate of evaporation from the specimen plate, including but not limited to a thin penetrable sheet that covers the specimen plate. The specimen plate seal can be made of any material that will retard evaporation from the specimen plate, including but not limited to plastic, cloth, rubber, wax paper, and cellophane. The specimen plate seal allows a liquid transferring tip to pass through it for control of the biochemical milieu of the specimen. A non-limiting example of such a specimen plate seal is the TomTec THINLID™ (Hamden, Conn.)

The present invention fulfills the need in the art for environmental chambers that combine (a) a plate space that can hold specimen plates of a variety of sizes, including but not limited to commercially available microplates, microscope slides, and biological microchips; (b) gas flow control; and (c) control of the temperature of the entire specimen plate. The environmental chamber of the present invention is a device for maintaining a specimen plate in an environmentally-controlled system while the plate is scanned by a fluorescence or luminescence system, or a cell screening or imaging system, including but not limited to the cell screening system described in U.S. patent applications Ser. No. 08/810,983 (Feb. 27, 1997) and U.S. Ser. No. 09/031,271 (Feb. 27, 1998). The chamber system is easily integrated into fluorescence and/or luminescence microscopy systems.

In one embodiment, the environmental chamber of the present invention comprises:

a. a chamber housing comprising a plate space comprising a plate holder sized to permit insertion of a specimen plate, wherein the specimen plate comprises the bottom of the chamber housing when it is inserted into the chamber;

b. at least one gas inlet port;

c. a lid assembly comprising:
1. a lid with a top and bottom surface, wherein the bottom surface overlays the plate space in the chamber housing when the lid is closed; and
2. a heater attached to the top or the bottom of the lid.

In this embodiment, heat is delivered to the specimen plate from the chamber lid. This unique heating solution bypasses the usual problems associated with the heating systems of existing environmental chamber systems. These problems include:

1) the necessity of a large amount of space to accommodate the large enclosures (typically 12" L×12" W×6" H) that are part of most of the commercially available environmental chambers, 2) the need to control the temperature of the large volume of gas contained within the large enclosures that are part of most of the commercially available environmental chambers, 3) the need to pre-heat the gas before delivering it to the chamber, 4) a drop in temperature above the objective relative to positions removed from the objective.

Preferably, the distance between the heater and the specimen plate is in the range of 0.5 inches to 1.5 inches.

In a preferred embodiment, the temperature is controlled via a temperature control system that uses a probe that is situated within or on the specimen plate, which is electrically connected via a probe lead to a temperature controller.

Most of the existing chambers described above are large to (1) create contact points with the condenser and (2) accommodate mechanical manipulators. In contrast, the environmental chamber of the present invention is designed to position a specimen plate for scanning by a fluorescence or luminescence system, or a cell screening or imaging system, which do not have condensers above the specimen plate, and generally do not use mechanical manipulators. Thus, the present device can be much smaller than prior environmental chambers, which is desirable for reasons including but not limited to meeting the demands of limited workspace, ease of user handling and cleaning, cost reduction, ease of integrating the chamber into existing devices, more rapid recovery to operating conditions after changing plates, and lower overall gas consumption.

The dimensions of the chamber of the invention range from between about 5 inches high×12 inches long×12 inches wide to about 0.5 inches high×1 inch long×1.5 inches wide.

In one embodiment, the chamber is custom-sized for commercially available microplates. In this embodiment, the chamber dimensions are approximately 1.5 inches H by about 6.5 inches W, by about 6.5 inches L, which provides a chamber volume that accommodates a single microplate.

In another embodiment, the chamber is custom-sized for commercially available chambered coverglass assemblies. In this embodiment, the chamber dimensions are approximately 0.8 inches H by about 2.0 inches W, by about 3.5 inches L, which provides a chamber volume that accommodates a single assembly.

In another embodiment, the chamber is custom-sized for commercially available microchips. In this embodiment, the chamber dimensions are approximately 0.7 inches H by about 2.0 inches W, by about 2.0 inches L, which provides a chamber volume that accommodates a single microchip.

In another embodiment, the chamber is custom-sized for multiple commercially available microplates. In this embodiment, the chamber dimensions are about 5 inches H×12 inches W×12 inches L, which provides a chamber volume that accommodates multiple microplates. In this embodiment, the lid, lid heater, and chamber housing are extended to cover all of the plates housed within the chamber.

It will be understood by one of skill in the art, that numerous modifications of the chamber can be made to accommodate multiple chambered coverglass assemblies and microchips, as well as a wide variety of numbers of such assemblies, microchips, or commercially available microplates, all of which are within the scope of the present invention.

The chamber and lid assembly can be made of any material compatible with required conditions for the maintenance of live cells. Such materials include, but are not limited to anodized aluminum, stainless steel, titanium, and plastics including but not limited to acrylic and acetal (DELRIN®).

In a most preferred embodiment, the chamber and lid assembly are constructed of aluminum. Existing chambers are made of acrylic. Aluminum is preferable to acrylic, as it does not transmit light and thus, use of an aluminum environmental chamber does not require the user to work in low room light conditions, as would otherwise be required in order to protect the fluorescence of the sample. Furthermore, aluminum is much less likely than acrylic to be damaged over time or during normal use.

In a preferred embodiment, the chamber further comprises a chamber gasket that seals the space between the specimen plate and the plate holder. The gasket may be made of any material suitable for use in providing a sealing means between the plate holder and the specimen plate, including but not limited to silicone rubber (e.g. polydimethyl siloxane).

In a further preferred embodiment, the chamber further comprises at least one gas outlet port, to allow gas to exit the chamber in a controlled fashion. Numerous other modifications can be made to more evenly distribute the gas, including but not limited to forcing the gas through a rotor or fan, as it enters the gas inlet space.

In a further preferred embodiment, the chamber further comprises at least one gas outlet port that removes gas from the plate space, as a further means to control the gas flow in the environmental chamber.

In further preferred embodiments, the chamber further comprises a lid cover with a top and bottom surface attached to the top surface of the lid. The lid cover is made from the same material as the rest of the chamber, preferably aluminum.

In a further preferred embodiment, the chamber further comprises a lid insulator affixed to the top surface of the lid cover. The lid insulator can be of any material suitable for improving the insulation of the environmental chamber, including but not limited to silicone rubber and epichlorohydrin (ECH) sponge rubber. Most preferably, the insulator comprises ECH sponge rubber.

In further embodiments, the chamber comprises at least one of a lid latch to fix the lid in a closed position over the chamber housing and a lid gasket affixed to the bottom surface of the lid to further optimize temperature and gas control. The gasket can be made of the same type of materials as the chamber gasket (see above).

In an alternative aspect, the gas pressure in the environmental chamber is controlled by a gas flow control system, which comprises at least one gas inlet port, which is connected to a controller which controls gas flow rate from a gas source.

In a preferred embodiment, carbon dioxide is maintained through direct delivery of an air-gas mixture, and humidity in the specimen plate is maintained by the use of a specimen plate seal. Such a specimen plate seal refers to any means to decrease the rate of evaporation from the specimen plate, including but riot limited to a thin penetrable sheet that covers the specimen plate. The specimen plate seal can be made of any material that will retard evaporation from the specimen plate, including but not limited to plastic, cloth, rubber, wax paper, and cellophane. The specimen plate seal allows a liquid transferring tip to pass through it for control of the biochemical milieu of the specimen. A non-limiting example of such a specimen plate seal is the TomTec THINLID™ (Hamden, Conn.)

In another preferred embodiment, humidity is maintained by bubbling the gas through water or buffer solution.

In a further preferred embodiment, the gas flow control system further comprises a chamber switch in the chamber housing to further control the gas flow rate into the chamber. In a further preferred embodiment, the gas flow control system further comprises a valve that is either integral to or connected to the controller.

In a most preferred embodiment, the gas flow control system and the temperature control system share the same controller.

In another embodiment, a specimen plate is inserted into the plate holder. The specimen plate can be any of the embodiments described above.

In another aspect, the present invention provides methods for utilizing the environmental chamber of the invention for cell-based analysis, including but not limited to cell-based screening, cell biological research, and cell-based diagnostics. The environmental chamber of the present invention is a system for maintaining specimen plates in an environmentally-controlled system while the plate is scanned by a fluorescence or luminescence system, or within a cell screening or imaging system.

The environmental chamber of the present invention can be custom-fitted within a fluorescence or luminescence system, or within a cell screening or imaging system, including but not limited to the cell screening system described in U.S. Pat. applications Ser. No. 08/810,983 (Feb. 27, 1997) and U.S. Ser. No. 09/031,271 (Feb. 27, 1998).

In a preferred embodiment of using the chamber for live cell screening, the specimen plate is setup within the plate space. In a most preferred embodiment, setup of the specimen plate includes the following steps:

1. Allow the temperature feedback control system to achieve a steady state.
2. Disable temperature feedback control, and lift chamber lid assembly.
3. Insert a specimen plate into the plate holder.
4. Place the feedback probe in contact with the bottom of the specimen plate.

If a microplate is used, then the probe is placed within and at the bottom of one of the wells.

5. Lower chamber lid assembly and enable feedback control.

In a further preferred embodiment of the method for live cell screening using the environmental chamber of the invention, solutions (ie: culture medium, reagents, test compounds, etc.) are added to or withdrawn from the specimen plate, as follows:

1. Disable temperature feedback control, and lift the chamber lid assembly.
2. Add or withdraw solution from the specimen plate.
3. Lower chamber lid assembly and enable feed back control.

The present invention may be better understood with reference to the accompanying examples that are intended for purposes of illustration only and should not be construed to limit the scope of the invention.

EXAMPLE OF THE PREFERRED EMBODIMENTS

Example 1

In a preferred embodiment (FIG. 1), an environmental control system comprises a tank (101) of 5% $CO_2$ gas (95% air), a flow and temperature controller (102), an environmental chamber (103), tubing (104) and wiring (105). Preferred embodiments of each of the components and their functions are discussed below.

Figure 2:
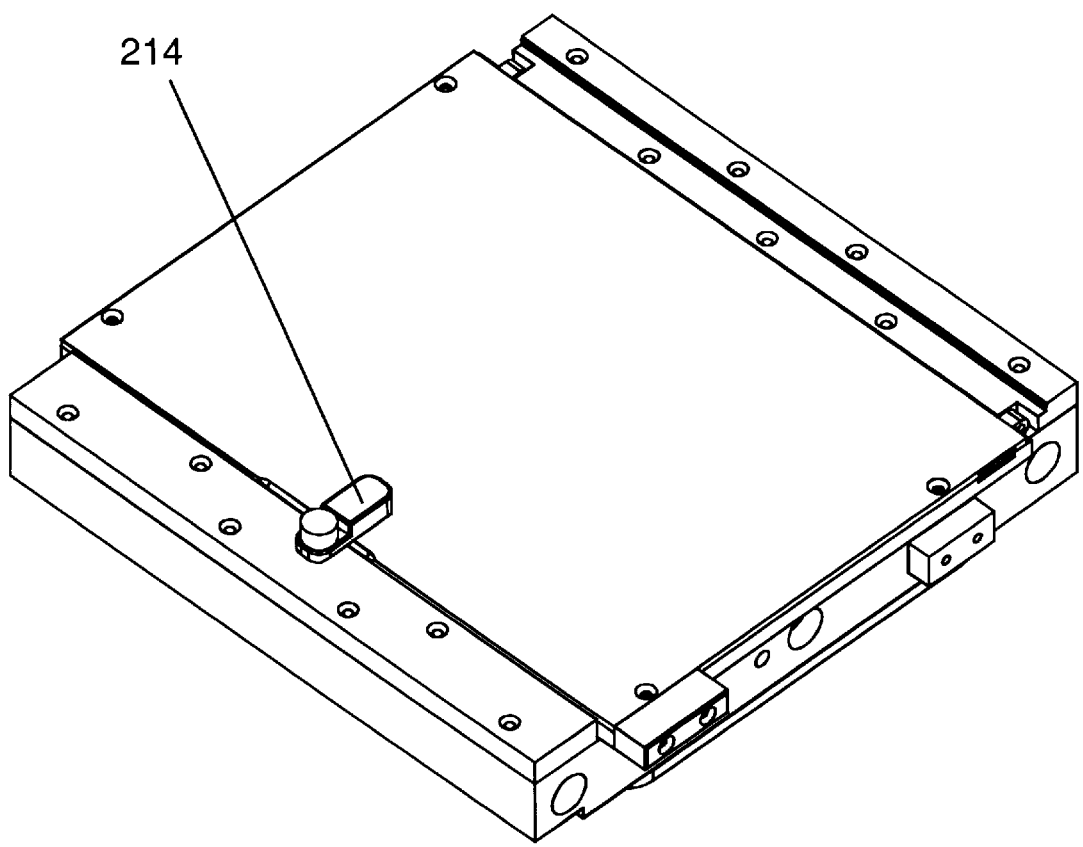
FIG. 2 is a top three quarter view of a preferred embodiment of the environmental chamber, showing the lid assembly in the open position.
Figure 3:
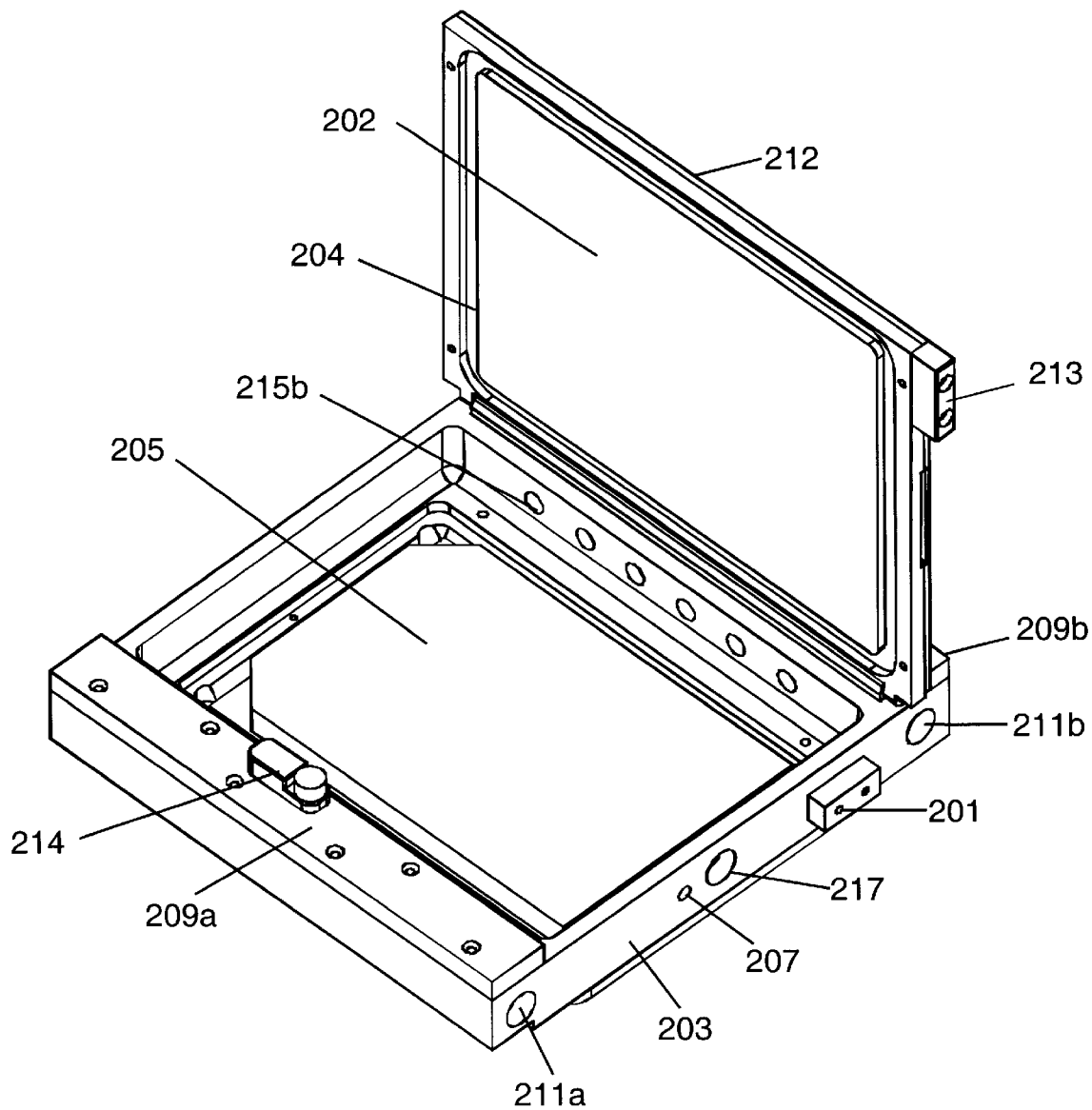
FIG. 3 is a top three-quarter view of a preferred embodiment of the environmental chamber, showing the lid assembly in the closed position.
Figure 4:
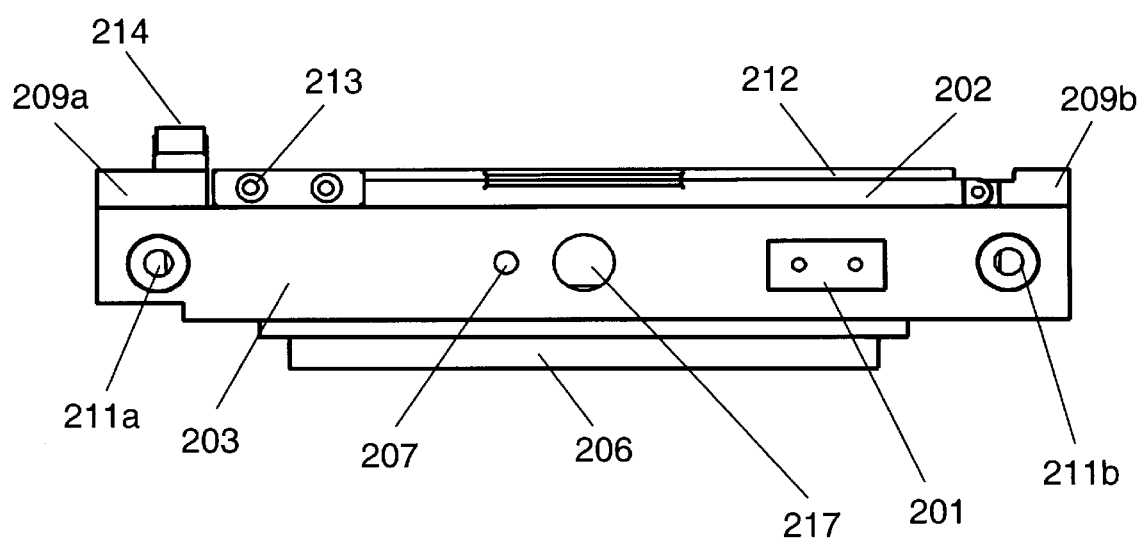
FIG. 4 is a side view of a preferred embodiment of the environmental chamber

Chamber (FIGS. 2–4)

The chamber consists of a number of custom and commercially available components.

Custom Components of the Chamber a) The chamber housing (FIG. 2) (203) is milled from a single block of aluminum and is ¾" high×6 7/16" wide×6 3/16" long . These dimensions are selected to yield a volume that is slightly larger than a commercially available microplate, while still being large enough to make chamber use practical. Three spaces exist within the housing: two smaller gas inlet spaces (situated beneath covers (209a, 209b)) and one larger plate space. Gas flows from the inlets (211a, 211b) to the inlet spaces, and continues through series of holes (215a and 215b) into the plate space. The gas exits through the outlet (217). The covers are part of the lid hinging and lid closing mechanisms. The top of the plate space is bounded by the lid (202) when the lid is in closed position (FIG. 3). The bottom of the plate space is open until a plate (205) and a chamber gasket (not shown) are inserted. The chamber gasket is a custom component made in-house from silicone elastomer. It seals the space between the plate (205) and the plate holder (206) that bounds the bottom of the chamber.

b) The lid assembly consists of the lid (202), lid cover (212), lid insulator (not shown), lid handle (213), and heater (not visible in figure). The lid and lid cover are each milled from single blocks of aluminum, and encapsulate the heater. Thus, in this preferred embodiment, the environmental chamber provides heat via its lid. This arrangement of custom lid components provides uniform heating of the entire microplate (described below). A thin foam rubber pad is affixed to the top side of the lid cover to insulate the lid. The lid can be fixed in a closed position by the swinging of the lid latch (214) (FIGS. 2 and 3) that pivots above one of the covers (209a). The latch works against the gentle compression force of the lid gasket (not shown) when the latch is swung into place. The lid gasket is a strip of commercially available silicone rubber that is shaped and fixed within the channel (204) that exists on the underside of the lid (202).

Figure 6A:
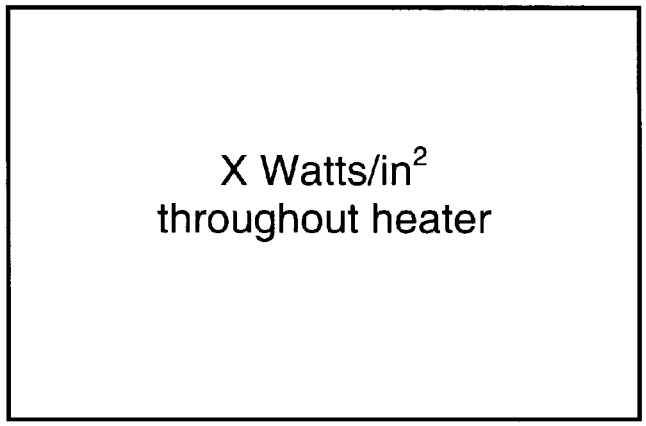
FIG. 6(A) Power density of one heater embodiment (B) Power density of a preferred heater embodiment.

In one embodiment, the power density of the heater is uniform throughout the heater (FIG. 6A). In a preferred embodiment (FIG. 6B), the power density of the heater along the edges of the heater (Region 2) is higher than the power density in the non-edge region of the heater (Region 1). The transition from region 2 to region 1 can be a step (sharp) change in power density, or a gradient of power density that increases from the heater edge to the heater center (ie: region 2 with an increased watts per square inch relative to the region 1).

Commerically Available Components of the Chamber

The RTD feedback probe, connectors, and tubing are commercially available. An edge of the aluminum RTD feedback probe casing is manually roughened during assembly to provide friction between the casing and well wall. A commercially available specimen plate seal (TomTec THIN-LID™ (Hamden, Conn.)) is affixed to the top of a microplate to maintain humidity within the wells of the plate.

Temperature Control System

The temperature control system consists of a number of custom and commercially available components.

In the preferred embodiment, the temperature control system consists of a typical process controller (502) (FIG. 5) that is mounted to the flow and temperature controller (102), a custom 25 Watt 24 V (rms) AC foil heater (106) that is fixed to the chamber lid (202), and an RTD feedback temperature probe (107) (See FIGS. 1 and 2). The temperature within the chamber is set through the front panel of the process controller. The actual (503) and set point (504) temperatures of the feedback probe are displayed on the process controller. The set point is set by the user via the function (506) and arrow (507) keys on the process controller display. Control is achieved through the automatic application of AC current to the heater for an appropriate fraction of the 15 second control period. After the system has achieved a steady-state the fraction is approximately one half under typical laboratory conditions (20° C.). The feedback probe is situated in a test well that is free of solution. The probe is held in place by gravity and friction. The size of the probe is dependent on the size of the wells in or on the specimen plate. The probe lead passes through a grommet (207) that is mounted in the chamber housing wall. The grommet is present to insulate the probe lead from the warm chamber housing wall. When the chamber lid is open the controller is manually set (505) to 'Stand-by Mode' by the user to disable the temperature feedback control. This action eliminates over-heating of the chamber lid. Preferably, the temperature feedback control is disabled automatically when the user opens the lid.

One difference between most of the existing chambers and the environmental chamber of the present invention is the temperature control system. While most of the existing chambers only control the temperature of the gas or the stage, the present environmental chamber controls the temperature of the specimen plate to within 1° C. over most of its area. This control is achieved with two improvements over the existing chambers: direct temperature sensing from within or on a specimen plate, and even delivery of heat from a proximal planar surface (the chamber lid). Lid heating is unique among existing microscope chamber systems that deliver gas to a specimen. Lid heating eliminates the need for preheating of gas that is used by many prior devices. It also eliminates the uneven plate heating that is caused by the objective hole in the stage in systems where the stage is heated.

Gas Flow

Figure 5:
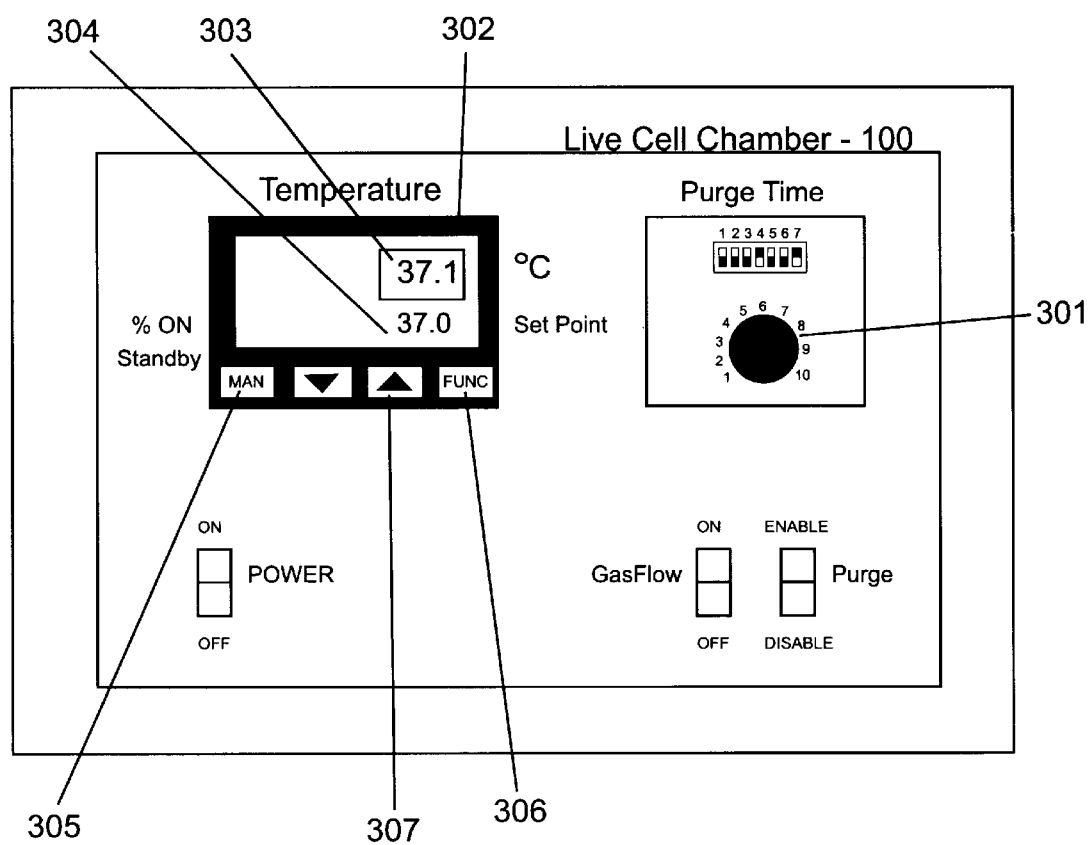
FIG. 5 shows a preferred embodiment of the front panel of the flow and temperature controller.

In the preferred embodiment, the standard rate of gas flow (250 ml/min) is set by a floating ball flow meter that is mounted to the controller. The chamber switch (201) (FIG. 2) detects the opening and closing of the lid which leads to the automatic ejection of room air from the chamber. The ejection event is referred to as "purging". The purge rate of gas flow (10 L/min) is achieved by bypassing the flow meter, and the duration of the purge event (0–10 sec) is set with the Purge Time control knob (501) (FIG. 5). The plate space (FIG. 2) is sealed by the lid (202) and chamber housing (203) gaskets (described above).

Gas Flow Rate and $CO_2$ Concentration Control

In a most preferred embodiment, the environmental chamber of the instant invention delivers air or a premixed gas to the chamber. The simplicity of this gas flow-through system ensures constant delivery of the correct concentration of $CO_2$ to the biological preparations. Most prior art environmental chambers do not maintain a pre-selected gaseous environment.

The gas tank (101) delivers a 5% $CO_2$/air mixture and a regulator delivers this gas at 10 psi to the controller (102). The flow and temperature controller is a custom device that is assembled from commercially available electronic, gas flow, and control system components. A representation of the front panel is shown in FIG. 5.

Example 2

Figure 7:
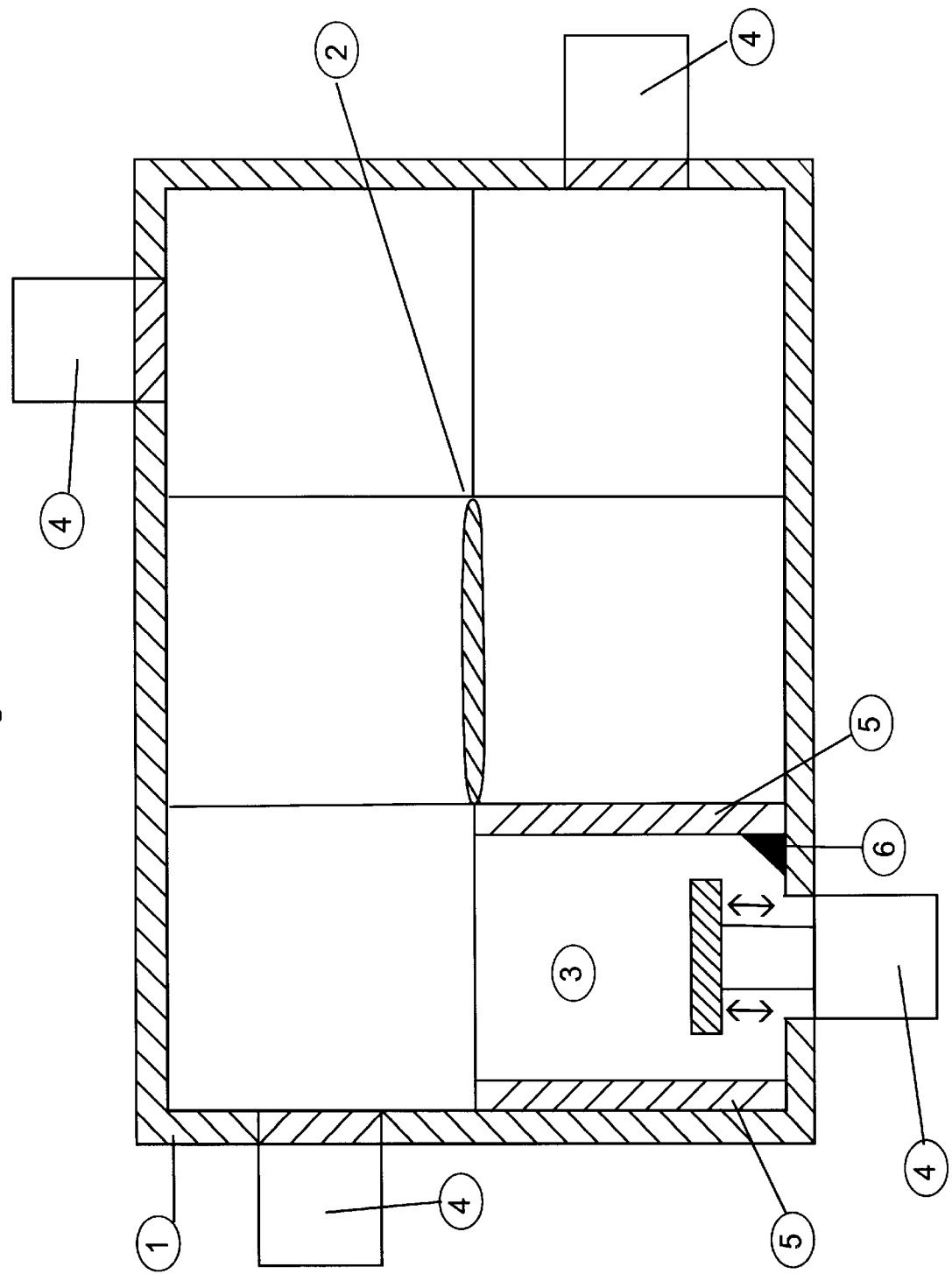
FIG. 7 is a drawing showing a multiple plate embodiment of the environmental chamber.

In a multiple plate embodiment of the present invention, the chamber is extended to accommodate space for 6 specimen plates (FIG. 7). One of these specimen plates is for the plate reader (3). One space is left open and does not contain a plate. Plates slide in and out of the plate reader space by means of plate pushers (4) that rotate plates from one position to the next, taking advantage of the one free space. A plate bumper (2) in the center guides the plates and prevents plate jams. A plate popper (5) is used to raise the plate in the reader to the level of the specimen plates in storage. A plate fixer (6) pushes on the corner of the plate when it is in the reader to fix it in X and Y directions in the same position from plate to plate. In this embodiment, the heater covers the complete 6-plate space. Alternatively, the heater may be designed to cover a subset of the plate spaces. It will be apparent to one of skill in the art that more or fewer plate spaces can be incorporated into the multiple plate embodiment using the teaching provided above.

Performance of One Embodiment of the Environmental Chamber of the Present Invention The results described below were obtained using an environmental chamber system (Example 1; FIGS. 1–5), with a chamber sized to hold a commercially available microplate, with a uniform power density heater. A 96-well plate was used for the following experiments.

A. Brief Descriptions of Procedures Used for Evaluation

1. Temperature Measurements 5 thermocouple probes were inserted into 5 representative wells. This thinness of the leads (36-guage) allowed chamber sealing with the lid closed.

2. pH Measurements: A narrow tip electrode was inserted into the wells. Control experiments documented the slow upward drift in pH values over time after the lid was raised. Data were corrected based on values obtained from these control experiments.

3. Media Evaporation Rates: Microplates were weighed to determine the volume of media present in the wells.

4. Internal Chamber Volume: Water was added to the sealed chamber until the inner volume was filled. The volume of added water was determined.

5. Live Cell Experiments: Typical mammalian cells (Chinese Hamster Ovary) were incubated in the chamber for 4 hours at 37° C. Morphological changes were monitored and recorded with the cell screening system described in U.S. patent applications Ser. No. 08/810,983 (Feb. 27, 1997) and U.S. Ser. No. 09/031,271 (Feb. 27, 1998).

B. Results of Experiments 1–4

| TEMPERATURE | |
|---|---|
| hours time scale variation[1] | 0.1° C. |
| minutes time scale variation[1] | ±0.05° C. |
| seconds time scale variation[1] | not detected |
| over entire plate (setpoint = 37.0° C.) | 37.0 ± 2.0° C. |
| edge wells excluded | 37.0 ± 1.0° C. |
| pH OF MAMMALIAN CELL CULTURE MEDIA | |
| hours time scale variation[2] | ±0.02 pH units |
| spatial variation[2] over entire plate | ±0.05 pH units |
| MEDIA EVAPORATION RATE | |
| with specimen plate seal | 1.3%/hr |
| without specimen plate seal | 4.2%/hr |
| INTERNAL CHAMBER VOLUME | 350 ml |

[1]Temperature variation defined as observed deviation from a set point; the maximum deviation is used for the documented upper and lower limits.
[2]pH value variation defined as observed deviation from the mean observed value; the maximum deviation is used for the documented upper and lower limits.

Figure 6B:
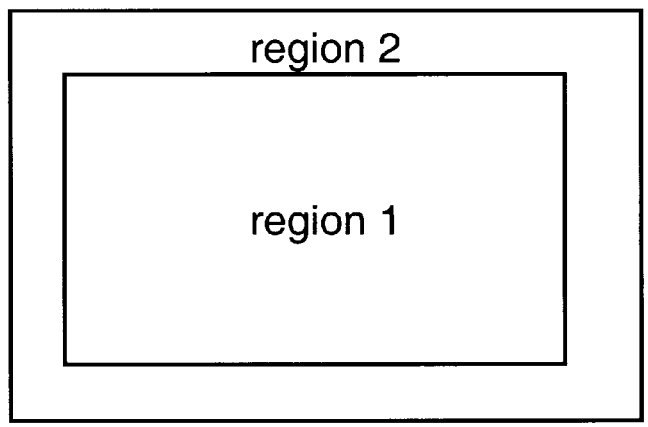

The heater design shown in FIG. 6B can be used to reduce the range of temperatures over the entire plate resulting from variability of the temperature of edge wells when the uniform power density heater shown in FIG. 6A is used.

C. Results of Experiment 5

Cells incubated in the environmental chamber of the present invention showed no aberrant morphological changes during the four hour experiment. The cells maintained an elongated and well-spread shape after 1.8 hours and 4.2 hours of incubation which is a basic indication of maintenance of cell health. The general cell shapes did not change over the 4.2 hours except for the one cell division that was observed; a larger, and more intense circular cell became two daughter cells. The rounding of a cell during cell division is typical.

SUMMARY

The present invention fulfills the need in the art for environmental chambers that combine (a) a plate space that can hold specimen plates of a variety of sizes, including but not limited to commercially available microplates, microscope slides, and biological microchips; (b) gas flow control; and (c) control of the temperature of the entire specimen plate. The environmental chamber of the present invention is a system for maintaining specimen plates in an environmentally-controlled system while the plate is scanned by a fluorescence or luminescence system, including but not limited to a cell screening or imaging system.

The environmental chamber of the present invention can be custom-fitted within a cell screening or imaging system, including but not limited to that described in U.S. patent applications Ser. No. 08/810,983 (Feb. 27, 1997) and U.S. Ser. No. 09/031,271 (Feb. 27, 1998), which is a table top instrument that includes optics for subcellular resolution of luminescent and fluorescent signals from many cells in a well. Images of cells are recorded and analyzed with the included camera, Pentium-based PC, and powerful software packages.

The present invention is not limited by the aforementioned particular preferred embodiments. It will occur to those ordinarily skilled in the art that various modifications may be made to the disclosed preferred embodiments without diverting from the concept of the invention. All such modifications are intended to be within the scope of the present invention.

We claim:

1. An environmental chamber for holding specimen plates comprising:
   a. a chamber housing comprising a plate space comprising a plate holder sized to permit insertion of a specimen plate, wherein the specimen plate comprises the bottom of the chamber housing when it is inserted into the chamber;
   b. at least one gas inlet port;
   c. a lid assembly comprising:
      1. a lid with a top and bottom surface, wherein the bottom surface overlays the plate space in the chamber housing when the lid is closed; and
      2. a heater attached to the top or the bottom of the lid.

2. The chamber of claim 1, wherein the plate space further comprises at least one gas inlet space, wherein the at least one gas inlet port feeds into the gas inlet space.

3. The chamber of claim 1 wherein the specimen plate is inserted into the plate space.

4. The chamber of claim 3 further comprising a specimen plate seal.

5. The chamber of claim 1 further comprising at least one gas outlet port.

6. The chamber of claim 1 further comprising a lid cover with a top and bottom surface attached to the top surface of the lid.

7. The chamber of claim 1 further comprising a lid insulator affixed to the top surface of the lid cover.

8. The chamber of claim 1 further comprising a lid latch to fix the lid in a closed position over the chamber housing.

9. The chamber of claim 1 further comprising a lid gasket affixed to the bottom surface of the lid.

10. The chamber of claim 1 wherein the chamber housing and the lid are aluminum.

11. An environmental control system comprising
   a. the environmental chamber of claim 1; and
   b. a temperature control system comprising
      1. a controller connected to the heater;
      2. a feedback probe; and
      3. a probe lead connecting the feedback probe and the controller.

12. An environmental control system comprising
   a. the environmental chamber of claim 1, and
   b. a gas flow control system comprising:
      1. a gas source connected to the at least one gas inlet port; and
      2. a controller connected to the gas source.

13. The environmental control system of claim 12 wherein the gas flow control system further comprises a chamber switch in the chamber housing to purge the chamber.

14. The environmental control system of claim 12 further comprising a valve that is either integral to or connected to the controller.

15. The environmental control system of claim 11 further comprising a gas flow control system comprising
   a. a gas source connected to the at least one gas inlet port; and
   b. a controller connected to the gas source.

16. The environmental control system of claim 15 wherein the gas flow control system further comprises a chamber switch in the chamber housing to purge the chamber.

17. The environmental control system of claim 15 further comprising a valve that is either integral to or connected to the controller.

18. An improved method for live cell analysis, comprising
   a. providing a specimen plate containing cells to be analyzed;
   b. providing the environmental chamber of claim 1;
   c. inserting the specimen plate into the plate space in the environmental chamber; and
   d. controlling gas flow to the specimen plate and temperature of the specimen plate during the live cell analysis.

19. An improved method for live cell analysis, comprising
   a. providing a specimen plate containing cells to be analyzed;
   b. providing the environmental chamber of claim 15;
   c. inserting the specimen plate into the plate space in the environmental chamber; and
   d. controlling the gas flow to the specimen plate and the temperature of the specimen plate during the live cell analysis.

20. The method of claim 19 wherein the feedback probe is in contact with the top or bottom surface of the specimen plate.

* * * * *